(12) United States Patent
Brewer et al.

(10) Patent No.: US 9,700,371 B2
(45) Date of Patent: Jul. 11, 2017

(54) ELECTROSURGICAL SYSTEM

(75) Inventors: Robert J. Brewer, Newport (GB);
Robert E. Gadsden, Berkshire (GB);
Robert C. Humble, Monmouthshire (GB); Michael David Newton, Newport (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 866 days.

(21) Appl. No.: 13/016,221

(22) Filed: Jan. 28, 2011

(65) Prior Publication Data
US 2011/0202050 A1 Aug. 18, 2011

Related U.S. Application Data

(60) Provisional application No. 61/282,379, filed on Feb. 1, 2010.

(30) Foreign Application Priority Data

Feb. 1, 2010 (GB) .................................. 1001640.0

(51) Int. Cl.
*A61B 18/12* (2006.01)
*A61B 18/14* (2006.01)
*A61B 18/00* (2006.01)

(52) U.S. Cl.
CPC .. *A61B 18/148* (2013.01); *A61B 2018/00589* (2013.01); *A61B 2018/00625* (2013.01);
(Continued)

(58) Field of Classification Search
CPC ........ A61B 18/148; A61B 2018/00589; A61B 2018/00625; A61B 2018/00958;
(Continued)

(56) References Cited

U.S. PATENT DOCUMENTS 4,438,766 A * 3/1984 Bowers ........................... 606/37
5,312,401 A * 5/1994 Newton et al. .................. 606/46
(Continued)

FOREIGN PATENT DOCUMENTS

EP 1 932 487 6/2008
EP 1 977 706 10/2008
(Continued)

OTHER PUBLICATIONS

Search Report issued in International Application No. PCT/GB2011/000069, date of mailing Apr. 4, 2011.
(Continued)

*Primary Examiner* — Daniel Fowler
(74) *Attorney, Agent, or Firm* — Nixon & Vanderhye PC

(57) ABSTRACT

An electrosurgical system is provided for the treatment of tissue, the system comprising an electrosurgical generator (1) and an instrument (3) comprising an instrument shaft (10) having a longitudinal axis, and an electrode assembly (12) at one end of the shaft. The electrode assembly (12) comprises a first tissue treatment electrode (11), a second tissue treatment electrode (14), and first and second return electrodes (24, 25) electrically insulated from the first and second tissue treatment electrodes by means of insulation members (12, 15). The first and second tissue treatment electrodes (11, 14) each have an exposed surface for treating tissue, the exposed surface of the first tissue treatment electrode (11) being such as to treat tissue disposed on the longitudinal axis, and the exposed surface of the second tissue treatment electrode (14) being such as to treat tissue disposed laterally of the longitudinal axis. The instrument has a first set of connections (62A, 62C) by which the first tissue treatment electrode (11) can be placed in circuit with the first return electrode (24) such that, in use, a current path is established between the first tissue treatment electrode
(Continued)

Figure 1:
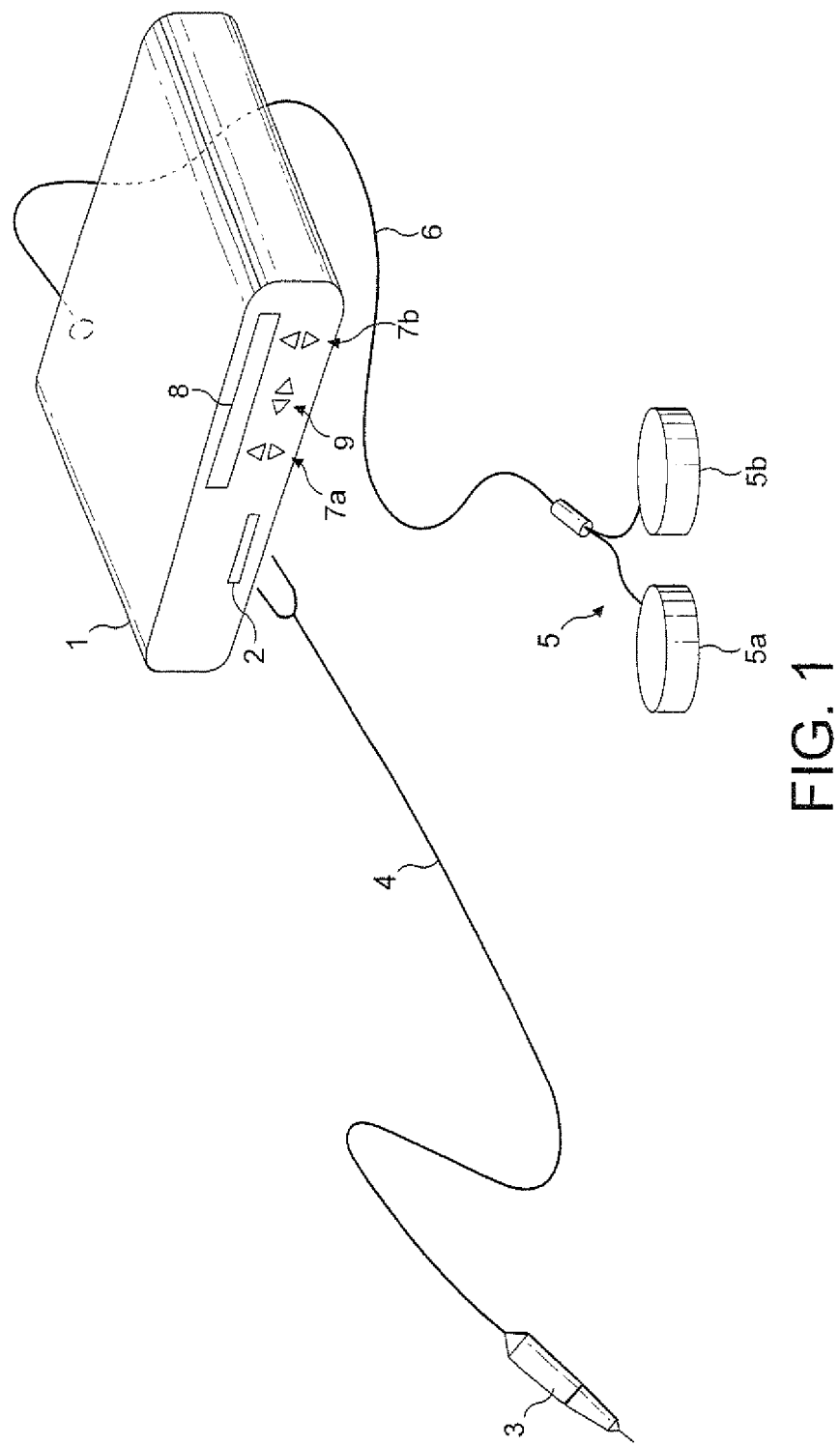

(11) and the first return electrode (24). The instrument has a second set of connections (62B, 62D) by which the second tissue treatment electrode (14) can be placed in circuit with the second return electrode (25) such that, in use, a current path is established between the second tissue treatment electrode (14) and the second return electrode (25).

18 Claims, 6 Drawing Sheets

(52) U.S. Cl.
CPC ........... *A61B 2018/00958* (2013.01); *A61B 2018/124* (2013.01); *A61B 2018/126* (2013.01); *A61B 2018/1467* (2013.01); *A61B 2018/1472* (2013.01); *A61B 2218/007* (2013.01)

(58) Field of Classification Search
CPC ........ A61B 2018/124; A61B 2018/126; A61B 2018/1467; A61B 2018/1472; A61B 2218/007
USPC .............................................. 606/27, 34, 41
See application file for complete search history.

(56) References Cited

U.S. PATENT DOCUMENTS

| | | | |
|---|---|---|---|
| 5,558,673 A * | 9/1996 | Edwards et al. | 606/41 |
| 5,697,909 A * | 12/1997 | Eggers et al. | 604/114 |
| 6,117,109 A | 9/2000 | Eggers et al. | |
| 6,152,923 A | 11/2000 | Ryan | |
| 6,960,204 B2 * | 11/2005 | Eggers et al. | 606/32 |
| 2003/0009164 A1 * | 1/2003 | Woloszko et al. | 606/41 |
| 2003/0040744 A1 * | 2/2003 | Latterell et al. | 606/48 |
| 2003/0045870 A1 | 3/2003 | Madsen | |
| 2004/0024398 A1 * | 2/2004 | Hovda et al. | 606/41 |
| 2009/0171352 A1 | 7/2009 | Sutter | |
| 2010/0010485 A1 | 1/2010 | West, Jr. | |
| 2010/0152726 A1 | 6/2010 | Cadouri et al. | |

FOREIGN PATENT DOCUMENTS

| | | |
|---|---|---|
| JP | 2000-512526 | 12/1997 |
| JP | 2003-500099 | 11/2000 |
| WO | WO 00/71043 | 11/2000 |

OTHER PUBLICATIONS

Written Opinion of the International Searching Authority for PCT/GB2011/000069.
Search Report issued in Priority Application No. GB1001640.0, Date of Search: May 24, 2010.
Japanese Office Action Patent Application No. 2012-550504; dated Sep. 30, 2014.
English language translation of Japanese Office Action for corresponding Japanese Patent Application No. 2012-550504; dated Sep. 30, 2014.
Patent Examination Report No. 1 issued in corresponding Australian Patent Application No. 2011209570 on Feb. 13, 2015.
Japanese Office Action Patent Application No. 2015-195601 dated Sep. 6, 2016.
English translation of Japanese Office Action for corresponding Japanese Application No. 2015-195601 dated Sep. 6, 2016.

* cited by examiner

ELECTROSURGICAL SYSTEM

This application claims priority to United Kingdom Application No. 1001640.0, filed 1 Feb. 2010 and claims the benefit of U.S. Provisional Application No. 61/282,379, filed 1 Feb. 2010, the entire contents of which are hereby incorporated by reference.

This invention relates to an electrosurgical system for the treatment of tissue. Such systems are commonly used for the vaporisation and/or coagulation of tissue in surgical intervention, most commonly in "keyhole" or minimally invasive surgery, but also in "open" surgery.

It is often the case that, during a surgical procedure, the surgeon is required to remove a first instrument and insert a second instrument, in order to achieve a particular tissue effect. The present invention attempts to provide an electrosurgical system having a surgical instrument that can be used in more than one manner, so as to reduce the number of times that an alternative instrument needs to be used.

Accordingly, an electrosurgical system is provided for the treatment of tissue, the system comprising a generator for generating radio frequency power, and an electrosurgical instrument, the generator comprising;

(i) a radio frequency output stage having at least a pair of radio frequency output lines, (ii) a power supply coupled to the output stage for supplying power to the output stage, the power being sufficient to effect the electrosurgical vaporisation of tissue; and (iii) a controller capable of varying a radio frequency signal supplied to the radio frequency output lines;

the electrosurgical instrument comprising;

an instrument shaft, and an electrode assembly at one end of the shaft, the electrode assembly comprising a first bipolar electrode pair comprising a first tissue treatment electrode and a first return electrode electrically insulated therefrom by means of a first insulation member, and a second bipolar electrode pair comprising a second tissue treatment electrode and a second return electrode electrically insulated therefrom by means of a second insulation member, the first and second bipolar electrode pairs each having a different characteristic;

the system further including a switch means and a switching circuit operable in response to the switch means to vary the connections between the radio frequency output lines and the first and second tissue treatment electrodes such that, in a first configuration, the first tissue treatment electrode is placed in circuit with the first return electrode so as to treat tissue adjacent to the first electrode pair, and, in a second configuration, the second tissue treatment electrode is placed in circuit with the second return electrode so as to treat tissue adjacent to the second electrode pair, the system being such that at least the first tissue treatment electrode is capable of the vaporisation of tissue.

By providing first and second bipolar electrode pairs, each pair having its own individual characteristic, the electrode pairs can be optimised for performing different to functions, as opposed to having only one bipolar electrode pair that needs to perform all functions. Where prior art electrosurgical systems are provided with more than one active (tissue treatment) electrode, they normally still have to share a common return electrode. In the present invention, there is provided four electrodes, two active electrodes and two return electrodes, forming first and second discrete electrode pairs, both optimised for their particular function. Prior art systems known to the applicant involving multiple electrode pairs are generally instruments only capable of generating lesions. In contrast, the present invention is capable of the vaporisation of tissue, from at least one of the bipolar electrode pairs, and preferably both pairs.

According to one convenient arrangement, the first and second bipolar electrode pairs are such that the first bipolar electrode pair is adapted to perform the vaporisation of tissue adjacent thereto, and the second bipolar electrode pair is adapted to perform the coagulation of tissue adjacent thereto. Thus one bipolar electrode pair is optimised for tissue vaporisation, while the other bipolar electrode pair is optimised for tissue coagulation. Conveniently, the exposed surface area of the first tissue treatment electrode is less than the exposed surface area of the second tissue treatment electrode. This helps to make the first electrode pair efficient for tissue vaporisation, and the second electrode pair efficient for tissue coagulation. Additionally or alternatively, the spacing between the first tissue treatment electrode and the first return electrode is less than the spacing between the second tissue treatment electrode and the second return electrode. This likewise helps to make the first electrode pair efficient for tissue vaporisation, and the second electrode pair efficient for tissue coagulation.

According to an alternative arrangement, the first and second tissue treatment electrodes are such that they each have an exposed surface for treating tissue, the exposed surface of the first tissue treatment electrode being such as to treat tissue disposed on the longitudinal axis of the shaft, and the exposed surface of the second tissue treatment electrode being such as to treat tissue disposed laterally of the longitudinal axis of the shaft. This optimises one pair for treating tissue disposed on the longitudinal axis (an "end-effect instrument"), and the other pair for treating tissue laterally of said longitudinal axis (a "side-effect instrument").

Conveniently, the first tissue treatment electrode protrudes through an aperture in the end of the shaft, while the second tissue treatment electrode conveniently protrudes through an aperture in the side of the shaft. By providing both an end-effect instrument and a side-effect instrument in one device, the present invention allows a surgeon to perform different surgical actions with the same instrument, as opposed to withdrawing a first instrument and inserting a second. By using the first tissue treatment electrode, the surgeon has an end-effect instrument, while using the second tissue treatment electrode provides the surgeon with a side-effect instrument. The surgeon can switch between these two modes of operation without needing to withdraw the instrument from the surgical site.

According to a further alternative arrangement, the first and second bipolar electrode pairs are such that the first bipolar electrode pair is adapted to perform the fine treatment of tissue adjacent thereto, and the second bipolar electrode pair is adapted to perform the bulk treatment of tissue adjacent thereto. This provides one electrode pair for fine dissection and coagulation work, and an alternative electrode pair for bulk tissue removal or bulk coagulation, again with the same instrument and without the surgeon needing to withdraw a first instrument and insert a second. Conveniently, the exposed surface area of the first tissue treatment electrode is less than the exposed surface area of the second tissue treatment electrode. Additionally or alternatively, the spacing between the first tissue treatment electrode and the first return electrode is less than the spacing between the second tissue treatment electrode and the second return electrode. These features make one electrode pair suitable for fine tissue work, and the other suitable for bulk tissue treatment.

The electrosurgical instrument is preferably provided with a suction lumen extending along the length of the shaft. In this way, the instrument can be used to aspirate tissue and other debris away from the surgical site. Conveniently, the first tissue treatment electrode is provided with at least one aperture in communication with the suction lumen. Similarly, the second tissue treatment electrode is conveniently provided with at least one aperture in communication with the suction lumen.

The electrosurgical system includes the switch means by which the surgeon can select either the first or second bipolar electrode pairs. Conveniently, the switch means comprises a footswitch, although as an alternative the switch means conceivably comprises a handswitch carried on the electrosurgical instrument. Alternatively, the switch means can be located on the generator. The switch means activates the to switching circuit, which is conveniently a part of the generator, although as an alternative the switching circuit is conceivably a part of the electrosurgical instrument.

In a first arrangement, the generator and electrosurgical instrument are such that the instrument is operable in a conductive fluid, with the conductive fluid completing the current path between the tissue treatment electrodes and the one or more return electrodes. This means that the system operates to perform what is known as "underwater" electrosurgery, in which the conductive site is immersed in a conductive fluid such as saline, and the electrodes operate immersed in said conductive fluid. An example of this type of electrosurgical system is given in our earlier U.S. Pat. No. 6,004,319. The power and voltage setting used by the generator are such that the conductive fluid surrounding the tissue treatment electrodes is vaporised when the electrosurgical instrument is operated in its cutting mode.

Alternatively, the generator and electrosurgical instrument are such that the instrument is operatable in a dry-field environment, with the tissue treatment electrodes and the one or more return electrodes being in direct contact with the tissue to be treated, and with the tissue completing the current path therebetween. An example of this type of electrosurgical system is given in our earlier U.S. Pat. No. 6,832,998. The power and voltage settings used by the generator are generally lower than in underwater electrosurgical systems, as the electrodes contact the tissue directly and there is no need to form a pocket of vaporised saline surrounding the electrode.

Figure 2:
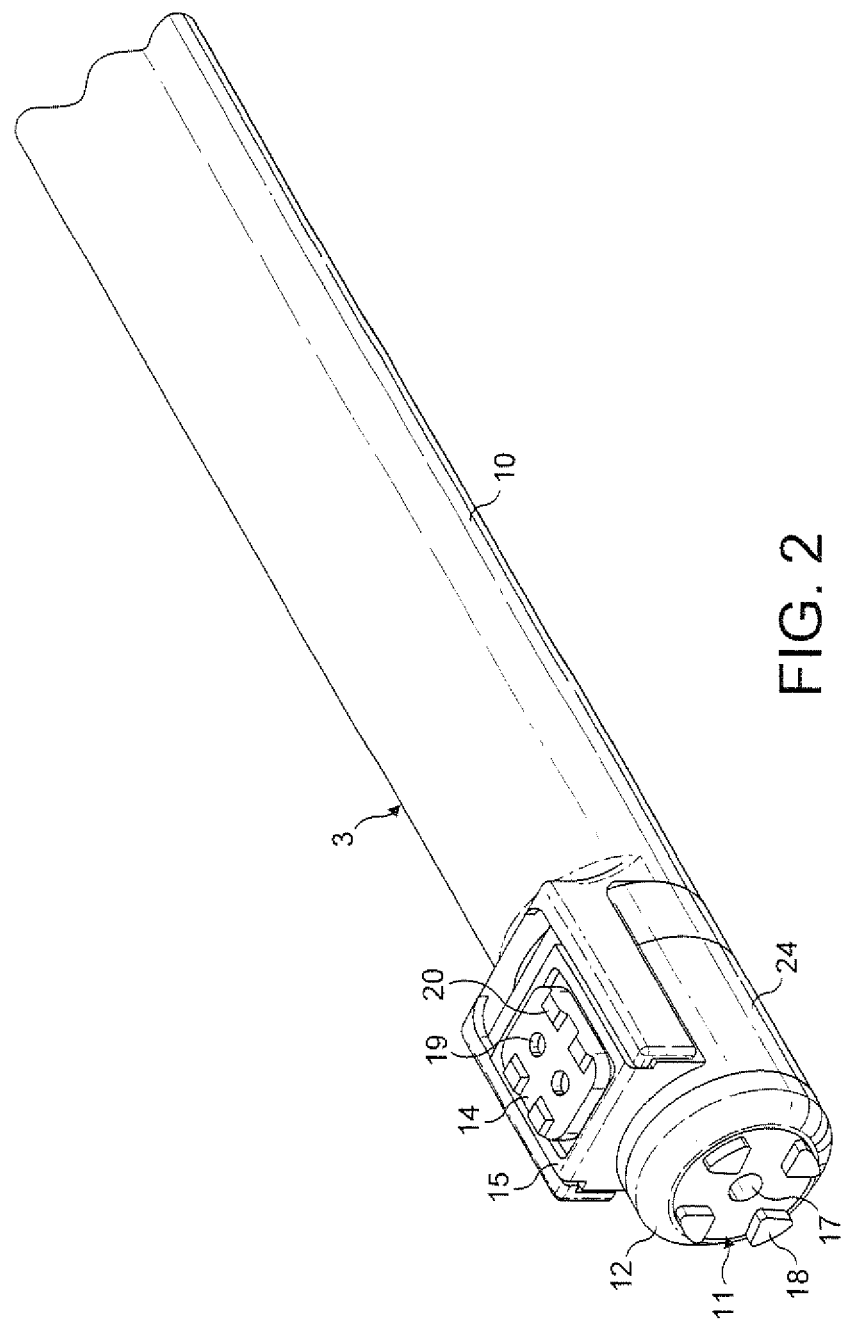
Figure 3:
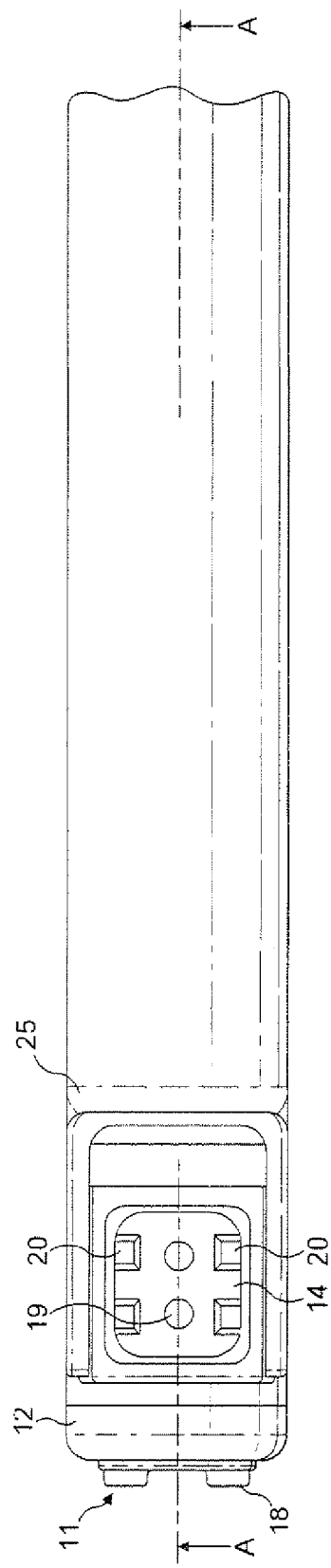
Figure 4:
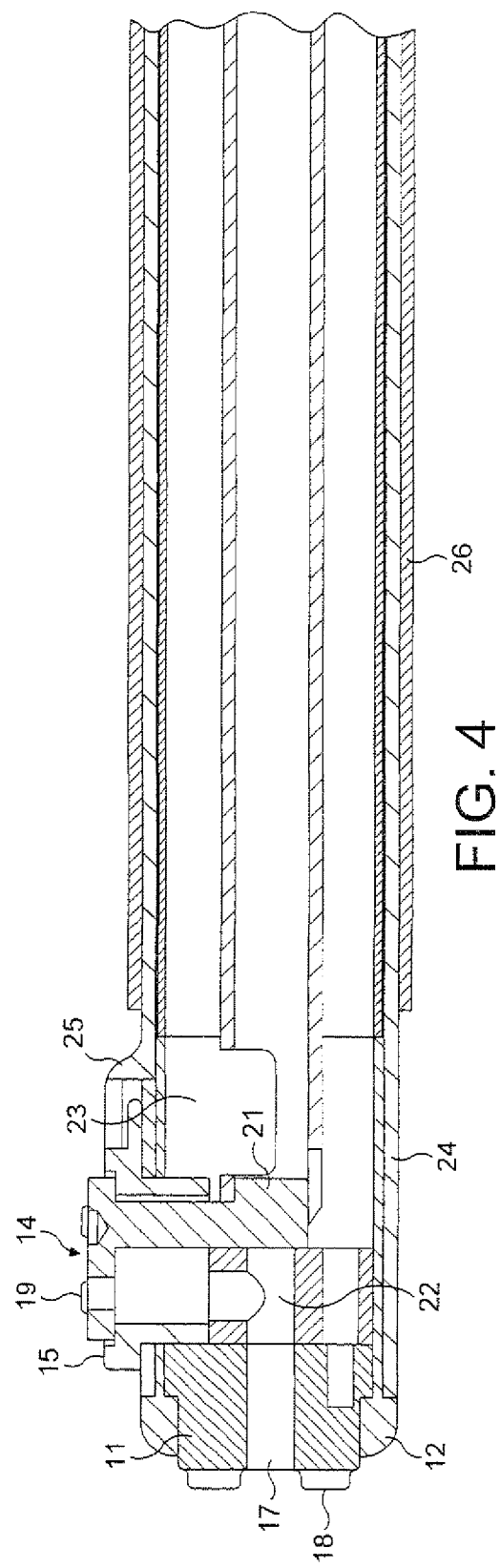
Figure 5A:
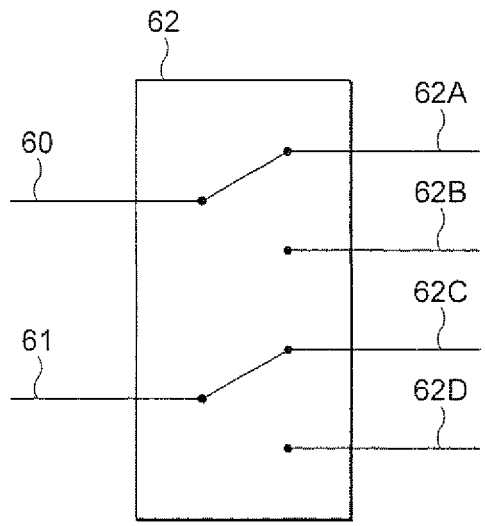
Figure 5B:
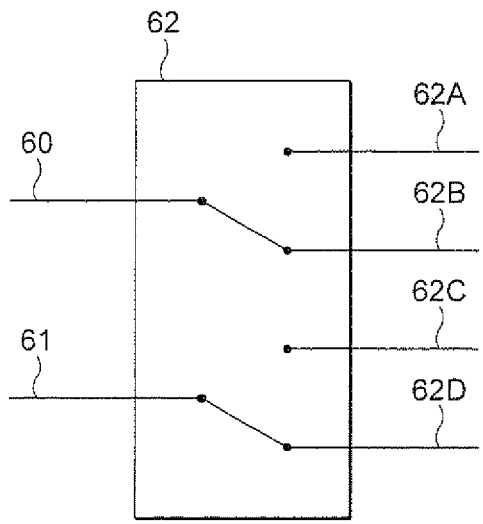
Figure 6:
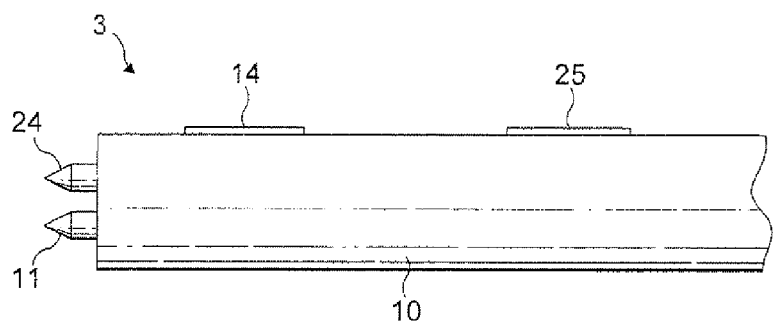
Figure 7:
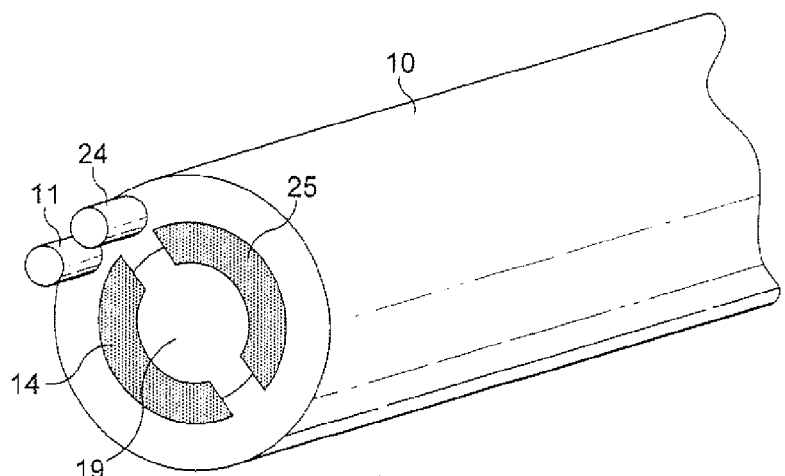
Figure 8:
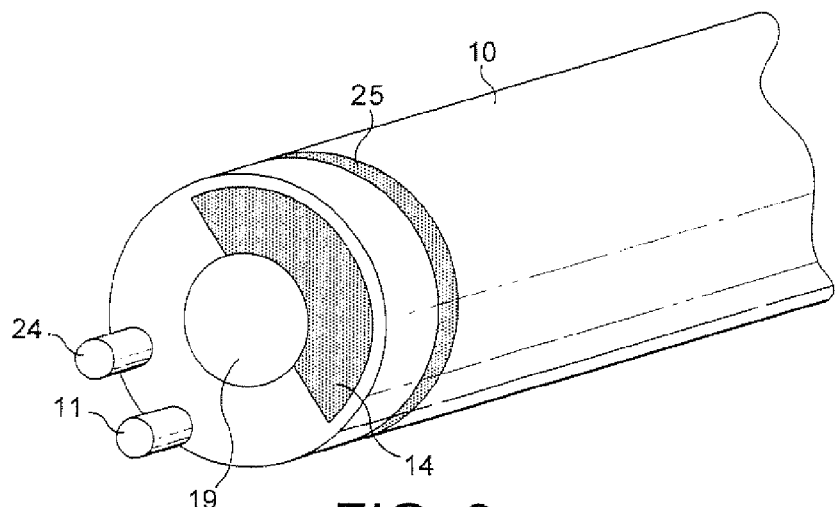

The invention will now be further described, by way of example only, with reference to the drawings, in which:

FIG. 1 is a schematic diagram of an electrosurgical system constructed in accordance with the present invention, FIG. 2 is a perspective view of an electrosurgical instrument constructed in accordance with the present invention, and capable of being used in the system of FIG. 1, FIG. 3 is a plan view of the electrosurgical instrument of FIG. 2, FIG. 4 is a cross-section of the electrosurgical instrument of FIG. 3, taken on the line A-A, FIGS. 5A and 5B are schematic block diagrams of the output stage of the electrosurgical generator of FIG. 1, shown in different stages of operation, FIG. 6 is a schematic side view of an alternative embodiment of electrosurgical instrument constructed in accordance with the present invention, and capable of being used in the system of FIG. 1, FIG. 7 is a schematic perspective view of a further alternative embodiment of electrosurgical instrument constructed in accordance with the present invention, and capable of being used in the system of FIG. 1, and FIG. 8 is a schematic perspective view of a further alternative embodiment of electrosurgical instrument constructed in accordance with the present invention, and capable of being used in the system of FIG. 1, Referring to the drawings, FIG. 1 shows electrosurgical apparatus including a generator 1 having an output socket 2 providing a radio frequency (RF) output, via a connection cord 4, for an instrument in the form of a handpiece 3. Activation of the generator 1 may be performed from the handpiece 3 via a control connection (not shown) in the cord 4, or by means of a footswitch unit 5 connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9 are provided as an alternative means for selection between the desiccation and vaporisation modes, or between the different tissue treatment electrodes as will be described subsequently.

The handpiece 3 comprises a shaft U) with tissue treatment electrodes at its distal end, as will be described below. FIGS. 2 to 4 show a first tissue treatment electrode 11 surrounded by a ceramic insulator 12 projecting through an aperture in the end of the shaft 10. A second tissue treatment electrode 14, surrounded by a second ceramic insulator 15, projects through a lateral aperture in the side of the shaft 10. Both tissue treatment electrodes 11 and 14 are formed of tungsten or an alloy of tungsten and platinum. The first tissue treatment electrode 11 is provided with a suction aperture 17, and has projections 18 at each of its corners. Similarly, the tissue treatment electrode 14 is provided with a suction aperture 19, and has projections 20 at each of its corners. The projections 18 and 20 are provided to concentrate the electric field at each of the corners of the tissue treatment electrodes 11 and 14. The projections 18 and 20 also serve to create a small separation between the planar surface of the tissue treatment electrodes 11 and 14 and the tissue to be treated. This allows conductive fluid to circulate over the planar surface, and avoids overheating of the electrodes 11 and 14 or the tissue.

The tissue treatment electrode 14 is located within the shaft 10 of the instrument 3 by means of a shaped keel portion 21, as described in our co-pending US patent application 2009/0048592. In summary, to assemble the instrument, the tissue treatment electrode 14 is lowered into a chamber 22 provided within the ceramic insulator 15. A suction tube 23 is then pushed forwards to locate over the keel portion 21 of the electrode 14 and secure it in place. Both the aperture 17 in the first tissue treatment electrode 11 and the aperture 19 in the second tissue treatment electrode 14 are in communication with the suction tube 23. In order to reduce the problems of vapour bubble production, and to assist with the removal of particulate material (such as tissue debris) from the region surrounding the tissue treatment electrodes 11 and 14, the suction tube 23 is connected to a suction pump (not shown) which can remove vapour bubbles via the shaft 10 of the instrument 3 through the apertures 17 and 19 respectively. The suction tube 23 is made of an electrically-conductive material such as stainless steel or gold-plated copper, and can also constitute means for electrically connecting one of the tissue treatment electrodes (typically the second tissue treatment electrode 14) to the generator 1.

A metallic ring 24 constitutes a first return electrode (associated with the first tissue treatment electrode 11). The ring 24 is located on the underside of the shaft 10, opposite the electrode 14. A second return electrode 25 (associated with the second tissue treatment electrode 14) is provided by the distal end portion of the shaft 10, and a polytetrafluoroethylene, a polyolefin, a polyester or ethylene tetrafluoroethylene sleeve 26 surrounds the proximal portion of the shaft 10 adjacent to the return electrode 25.

The RF generator 1 delivers an electrosurgical current to the instrument 3. The generator 1 includes means for varying the delivered output power to suit different electrosurgical requirements, such as vaporisation or coagulation. The generator 1 is typically as described in our earlier U.S. Pat. No. 6,293,942, with a switching circuit 62 (See FIGS. 5A and 5B) for switching the output lines from the generator to the electrosurgical instrument 3.

The switching circuit 62 comprises connections 60 and 61 from the generator 1, and output connections 62A, 62B, 62C and 62D respectively, The output connection 62A is connected to the first tissue treatment electrode 11, while the output connection 62C is connected to the first return electrode 24. Similarly, the output connection 62B is connected to the second tissue treatment electrode 14, while the output connection 62D is connected to the second return electrode 25. The operation of the electrosurgical system will now be described.

When the user of the system wishes to use the instrument 3 as an end-effect instrument, the user sends signals (via the footswitch unit 5, the handswitches on the instrument 3, or via the push buttons 9 on the generator 1) to set the switching circuit 62 into the condition shown in FIG. 5A. In this condition, the connections 60 and 61 from the generator 1 are connected to the output connections 62A and 62C, and hence to the first tissue treatment electrode 11 and first return electrode 24 respectively. RF power from the generator 1 is supplied to the electrodes 11 and 24, and hence tissue can be vaporised or coagulated as desired at the end of the shaft 10.

Alternatively, when the user of the system wishes to use the instrument 3 as a side-effect instrument, the user sends signals to set the switching circuit 62 into the condition shown in FIG. 5B. In this condition, the connections 60 and 61 from the generator 1 are connected to the output connections 62B and 62D, and hence to the second tissue treatment electrode 14 and the second return electrode 25 respectively. RF power from the generator 1 is supplied to the electrodes 14 and 25, and hence tissue can be vaporised or coagulated as desired laterally of the shaft 10. In this way, the surgeon can change between using the instrument 3 as either an end-effect instrument or as a side-effect instrument, merely by operating the footswitch 5, and without withdrawing the instrument 3 from the surgical site. The versatility provided by this arrangement allows for a single instrument effectively to perform the function of two instruments, as desired.

FIG. 6 shows an alternative embodiment of instrument, in which the first tissue treatment electrode 11 and the first return electrode 24 are located on the distal end face of the instrument, while the second tissue treatment electrode 14 and the second return electrode 25 are located on the side of the shaft 10. The electrodes 11 and 24 are designed for tissue vaporisation, being relatively pointed in shape and sited quite close to each other. In contrast, the electrodes 14 and 25 are designed for tissue coagulation, being relatively flat in shape, of a larger surface area than the electrodes 11 and 24, and sited at a greater distance one from the other, The choice of the electrode pairs 11 and 24 or 14 and 25 is made as previously described, using the footswitch unit 5, the push buttons 9 on the generator 1, or the handswitch buttons (not shown) on the instrument 3. These activate the switching circuit 62 to direct the output from the generator 1 to one or other of the bipolar electrode pairs 11 and 24 or 14 and 25. This instrument is intended to be used such that tissue vaporisation is carried out as an end-effect instrument (by the electrodes 11 and 24), while tissue coagulation is carried out as a side-effect instrument (using the electrodes 14 and 25). However, an RF cutting signal or RF coagulation signal can be supplied to either electrode pair. This means that the end-effect electrodes 11 and 24 can be used for precise tissue treatment (either vaporisation or coagulation), while the side-effect electrodes 14 and 25 can be used for bulk tissue treatment (either vaporisation or coagulation).

FIG. 7 shows an alternative embodiment in which all four electrodes 11, 24, 14 and 25 are located on the end face of the instrument 3. As before, the electrodes 11 and 24 present a smaller surface area to the tissue to be treated as compared with the electrodes 14 and 25. The electrodes 14 and 25 are substantially planar, and are sited either side of the suction aperture 19 in communication with the suction tube 23. As before, the switching circuit 62 directs either an RF cutting signal or an RF coagulation signal to whichever pair of electrodes is selected for use. In one method of operation, the electrodes 11 and 24 are used for tissue vaporisation, while the electrodes 14 and 25 are used for tissue coagulation. In another method of operation, the electrodes 11 and 24 are used for line tissue treatment, while the electrodes 14 and 25 are used for bulk tissue treatment. The proximity of the electrodes 14 and 25 to the suction aperture 19 permits tissue to be evacuated efficiently during bulk tissue removal.

Finally, FIG. 8 shows a further embodiment, in which the electrodes 11, 24 and 14 are located on the end face of the instrument, while the second return electrode 25 is located on the side of the shaft 10. As before, the characteristics of the electrode pair 11 and 24 are different from the electrode pair 14 and 25, allowing for different intended uses as previously described.

Alternative embodiments will be envisaged by those skilled in the art without departing from the scope of the present invention. For example, the electrosurgical instrument can also be used for delivering a blended power output. This is achieved by automatically alternating the output of the RF generator 1 between the coagulation and vaporisation power levels, so that more haemostasis is produced then is possible in the vaporisation mode. As a consequence, the speed of tissue debulking is reduced, but the increased haemostasis is useful when cutting or debulking vascular tissue structures.

Whereas the blended power output described above is delivered to one selected electrode pair, the blended power output can alternatively be delivered to different electrode pairs, as described in our earlier U.S. Pat. No. 6,966,907. In this arrangement, a blend of RF vaporisation and coagulation voltages is provided by the generator, with the RF cutting voltage being supplied to one pair of electrodes (typically the electrodes 11 and 24) and the RF coagulation voltage being supplied to the other pair of electrodes (typically the electrodes 14 and 25). In this way, simultaneous tissue cutting and coagulation is made possible, using bipolar electrode pairs designed specifically for each tissue effect.

Alternatively, the output of the RF generator I can be pulsed at the vaporisation power level, without cycled activation of the coagulation mode. This produces a less aggressive tissue vaporisation than occurs in the vaporisation mode, with a consequent reduction in both bubble formation and the risk of tissue charring. In a further alternative arrangement, an option is provided for both electrode pairs 11 and 24 and 14 and 25 to be simultaneously activated, for example so that the instrument 3 can deliver tissue treatment from both electrode pairs at the same time. It will be appreciated that some of these arrangements may require more sophisticated switching circuits than those described with reference to FIGS. 5A and 5B, but that these can be provided by those skilled in the art without undue difficulty.

The invention claimed is:

1. An electrosurgical system comprising:
a generator for generating radio frequency power,
an electrosurgical instrument, and
a switch and a switching circuit,
the generator comprising:
(i) a radio frequency output stage having at least a pair of radio frequency output lines,
(ii) a power supply coupled to the output stage for supplying power to the output stage, the power being sufficient to effect the electrosurgical vaporisation of tissue; and
(iii) a controller capable of varying a radio frequency signal supplied to the radio frequency output lines;
the electrosurgical instrument comprising:
an instrument shaft having a longitudinal axis and a distal end, and
an electrode assembly located at the distal end of the shaft, the electrode assembly comprising:
a first bipolar electrode pair comprising a first tissue treatment electrode and a first return electrode electrically insulated from the first tissue treatment electrode by means of a first insulation member, and
a second bipolar electrode pair different and separately operable from the first bipolar electrode pair and comprising a second tissue treatment electrode and a second return electrode electrically insulated from the second tissue treatment electrode by means of a second insulation member,
the first and second tissue treatment electrodes each having an exposed surface for treating tissue,
the exposed surface of the first tissue treatment electrode being disposed on the distal end of the shaft, so as to be capable of treating tissue disposed longitudinally of the longitudinal axis of the shaft, and
the exposed surface of the second tissue treatment electrode being disposed on a side of the instrument shaft, so as to be capable of treating tissue disposed laterally of the longitudinal axis of the shaft,
the first return electrode being located on the shaft such that it is diametrically opposite the second tissue treatment electrode in a plane perpendicular to the longitudinal axis;
the switching circuit being operable in response to the switch to vary connections between the radio frequency output lines and the first and second tissue treatment electrodes, such that, in a first configuration, the first tissue treatment electrode is placed in circuit with the first return electrode so as to treat tissue adjacent of the first electrode pair that is disposed longitudinally of the shaft, and, in a second configuration, the second tissue treatment electrode is placed in circuit with the second return electrode so as to separately treat tissue adjacent to the second electrode pair that is disposed laterally of the shaft,
at least the first tissue treatment electrode being capable of the vaporisation of tissue.

2. The electrosurgical system according to claim 1, wherein the first tissue treatment electrode protrudes through an aperture in the end of the shaft.

3. The electrosurgical system according to claim 1, wherein the second tissue treatment electrode protrudes through an aperture in the side of the shaft.

4. The electrosurgical system according to claim 1, including a suction lumen extending along the length of the shaft.

5. The electrosurgical system according to claim 4, wherein the first tissue treatment electrode is provided with at least one aperture in communication with the suction lumen.

6. The electrosurgical system according to claim 4, wherein the second tissue treatment electrode is provided with at least one aperture in communication with the suction lumen.

7. The electrosurgical system according to claim 1, wherein the switch comprises a footswitch.

8. The electrosurgical system according to claim 1, wherein the switch comprises a handswitch carried on the electrosurgical instrument.

9. The electrosurgical system according to claim 1, wherein the switching circuit is a part of the generator.

10. The electrosurgical system according to claim 1, wherein the switching circuit is a part of the electrosurgical instrument.

11. The electrosurgical system according to claim 1, wherein the generator and the electrosurgical instrument are such that the instrument is operable in a conductive fluid, with the conductive fluid completing the current path between the tissue treatment electrodes and the return electrodes.

12. The electrosurgical system according to claim 1, wherein the generator and electrosurgical instrument are such that the instrument is designed to be operated in a dry-field environment, with the tissue treatment electrodes and the return electrodes being in direct contact with the tissue to be treated, and with the tissue completing the current path therebetween.

13. A method of using an electrosurgical system comprising:
(i) providing a generator for generating radio frequency power, the generator comprising:
a radio frequency output stage having at least a pair of radio frequency output lines,
a power supply coupled to the output stage for supplying power to the output stage; and
a controller capable of varying a radio frequency signal supplied to the radio frequency output lines;
(ii) providing an electrosurgical instrument comprising:
an instrument shaft having a longitudinal axis and a distal end, and
an electrode assembly at the distal end of the shaft, the electrode assembly comprising:
a first bipolar electrode pair comprising a first tissue treatment electrode and a first return electrode electrically insulated from the first tissue treatment electrode by means of a first insulation member, and
a second bipolar electrode pair different and separately operable from the first bipolar electrode pair and comprising a second tissue treatment electrode and a second return electrode electrically insulated from the second tissue treatment electrode by means of a second insulation member, the first and second tissue treatment electrodes each having an exposed surface for treating tissue, the exposed surface of the first tissue treatment electrode being disposed on the distal end of the instrument shaft, so as to be capable of treating tissue disposed longitudinally of the longitudinal axis of the shaft, and the exposed surface of the second tissue treatment electrode being disposed on a side of the instrument shaft, so as to be capable of separately treating tissue disposed laterally of the longitudinal axis of the shaft, the first return electrode being located on the shaft such that it is diametrically opposite the second tissue treatment electrode in a plane perpendicular to the longitudinal axis; and at least one of:

(iii) manoeuvring the electrosurgical instrument, such that tissue to be treated is adjacent to the first tissue treatment electrode, (iv) operating a switch to vary connections between the radio frequency output lines and the first and second tissue treatment electrodes, such that the first tissue treatment electrode is placed in circuit with the first return electrode, (v) supplying power to the first tissue treatment electrode to effect the electrosurgical vaporisation of tissue adjacent to the first tissue treatment electrode longitudinally of the shaft, and (vi) manoeuvring the electrosurgical instrument, such that tissue to be treated is adjacent to the second tissue treatment electrode, (vii) operating the switch to vary the connections between the radio frequency output lines and the first and second tissue treatment electrodes, such that the second tissue treatment electrode is placed in circuit with the second return electrode, and (viii) supplying power to the second tissue treatment electrode to effect the electrosurgical vaporisation of tissue adjacent to the second tissue treatment electrode laterally of the shaft.

14. An electrosurgical system comprising:
a generator for generating radio frequency power,
an electrosurgical instrument, and
a switch and a switching circuit,
the generator comprising:
   (i) a radio frequency output stage having at least a pair of radio frequency output lines,
   (ii) a power supply coupled to the output stage for supplying power to the output stage, the power being sufficient to effect the electrosurgical vaporisation of tissue; and
   (iii) a controller capable of varying a radio frequency signal supplied to the radio frequency output lines;
the electrosurgical instrument comprising:
   an instrument shaft having a longitudinal axis and a distal end, and
   an electrode assembly located at the distal end of the shaft, the electrode assembly comprising:
      a first bipolar electrode pair comprising a first tissue treatment electrode and a first return electrode electrically insulated from the first tissue treatment electrode by means of a first insulation member, and
      a second bipolar electrode pair different and separately operable from the first bipolar electrode pair and comprising a second tissue treatment electrode and a second return electrode electrically insulated from the second tissue treatment electrode by means of a second insulation member,
      the first and second tissue treatment electrodes each having an exposed surface for treating tissue, the exposed surfaces of the first and second tissue treatment electrodes each being provided with at least one suction aperture,
      the exposed surface of the first tissue treatment electrode being disposed on the distal end of the shaft, so as to be capable of treating tissue disposed longitudinally of the longitudinal axis of the shaft, and
      the exposed surface of the second tissue treatment electrode being disposed on a side of the instrument shaft, so as to be capable of treating tissue disposed laterally of the longitudinal axis of the shaft;
      the first return electrode being located on the shaft such that it is diametrically opposite the second tissue treatment electrode in a plane perpendicular to the longitudinal axis;
the switching circuit being operable in response to the switch to vary connections between the radio frequency output lines and the first and second tissue treatment electrodes, such that, in a first configuration, the first tissue treatment electrode is placed in circuit with the first return electrode so as to treat tissue adjacent to the first electrode pair that is disposed longitudinally of the shaft, and, in a second configuration, the second tissue treatment electrode is placed in circuit with the second return electrode so as to separately treat tissue adjacent to the second electrode pair that is disposed laterally of the shaft,
at least the first tissue treatment electrode being capable of the vaporisation of tissue.

15. The electrosurgical system according to claim 14, wherein the exposed surfaces of the first and second tissue treatment electrodes are each a planar surface further provided with a plurality of projections for separating the planar surfaces of the first and second tissue treatment electrodes from the tissue to be treated, so as to allow conductive fluid to circulate over the planar surfaces, to thereby avoid overheating of the first and second tissue treatment electrodes or the tissue to be treated.

16. The electrosurgical system according to claim 15, wherein each of the projections concentrates at its location an electric field associated with a radio frequency signal supplied to the first or second tissue treatment electrodes.

17. The electrosurgical system according to claim 15, wherein the exposed planar surfaces of the first and second tissue treatment electrodes are each provided with a projection at each of its plurality of corners so as to concentrate at its plurality of corners an electric field associated with a radio frequency signal supplied to the first or second tissue treatment electrodes.

18. The electrosurgical system according to claim 17, wherein the exposed planar surfaces of the first and second tissue treatment electrodes are each provided with four corners.

* * * * *